(12) United States Patent
Renauld et al.

(10) Patent No.: US 7,846,652 B2
(45) Date of Patent: Dec. 7, 2010

(54) METHOD FOR IDENTIFYING A SUBSTANCE WHICH MEDIATES INTERACTION BETWEEN INTERLEUKIN 22 AND AN INTERLEUKIN 22 RECEPTOR

(75) Inventors: Jean-Christophe Renauld, Brussels (BE); Diane Lejeune, Brussels (BE); Laure Dumoutier, Brussels (BE)

(73) Assignee: Wyeth, Madison, NJ (US)

( * ) Notice: Subject to any disclaimer, the term of this patent is extended or adjusted under 35 U.S.C. 154(b) by 737 days.

(21) Appl. No.: 11/491,761

(22) Filed: Jul. 24, 2006

(65) Prior Publication Data

US 2006/0257408 A1 Nov. 16, 2006

Related U.S. Application Data

(60) Division of application No. 10/206,274, filed on Jul. 26, 2002, now abandoned, which is a continuation-in-part of application No. 09/915,735, filed on Jul. 26, 2001, now abandoned, which is a continuation-in-part of application No. 09/751,797, filed on Dec. 29, 2000, now Pat. No. 7,081,528, and a continuation-in-part of application No. 09/626,617, filed on Jul. 27, 2000, now abandoned.

(51) Int. Cl.
| | |
|---|---|
| *C12Q 1/00* | (2006.01) |
| *G01N 33/48* | (2006.01) |
| *G01N 33/50* | (2006.01) |
| *G01N 33/53* | (2006.01) |
| *G01N 33/68* | (2006.01) |
| *C07K 14/54* | (2006.01) |
| *C07K 14/705* | (2006.01) |
| *C07K 14/715* | (2006.01) |

(52) U.S. Cl. .................. 435/4; 435/6; 435/7.1; 435/7.2; 435/7.21; 435/69.1; 435/69.52

(58) Field of Classification Search ............... None
See application file for complete search history.

(56) References Cited

U.S. PATENT DOCUMENTS

| | | | |
|---|---|---|---|
| 6,159,694 A * | 12/2000 | Karras | ............... 435/6 |
| 6,274,710 B1 | 8/2001 | Dumoutier et al. | |
| 6,331,613 B1 | 12/2001 | Dumoutier et al. | |
| 6,359,117 B1 | 3/2002 | Dumoutier et al. | |
| 6,551,799 B2 | 4/2003 | Gurney et al. | |
| 6,939,545 B2 | 9/2005 | Jacobs et al. | |
| 7,307,161 B1 | 12/2007 | Jacobs et al. | |
| 7,638,604 B2 | 12/2009 | Li et al. | |
| 2003/0023033 A1 | 1/2003 | Dumoutier et al. | |

FOREIGN PATENT DOCUMENTS

| | | |
|---|---|---|
| WO | WO 00/70049 | 11/2000 |
| WO | WO 00/73457 | 12/2000 |
| WO | WO 00/77037 | 12/2000 |
| WO | WO 01/46422 | 6/2001 |
| WO | WO 02/10393 A2 | 2/2002 |
| WO | WO 03/010290 A2 | 2/2003 |

OTHER PUBLICATIONS

Blumberg et al., "Interleukin 20: Discovery, Receptor Identification, and Role in Epidermal function", Cell 104:9-19 (2001).
Crawley et al., "Interleukin-10 Stimulation of Phosphatidylinositol 3-Kinase and p70 S6 Kinase Is Required for the Proliferative but Not the Antiinflammatory Effects of the Cytokine", J. Biol. Chem 271:16357-16362 (1996).
Dumoutier et al., "Human interleukin-10-related T cell-derived inducible factor: Molecular cloning and functional characterization as an hepatocyte-stimulating factor", Proc. Natl. Acad. Sci. USA 97:10144-10149 (2000).
Finbloom et al., "IL-10 Induces the Tyrosine Phosphorylation of tyk2 and Jak1 and the Differential Assembly of STAT1α and STAT3 Complexes in Human T Cells and Monocytes", J. Immunol. 153:1079-1090 (1995).
Geng et al., "Monocyte deactivation by interleukin 10 via inhibition of tyrosine kinase activity and the Ras signaling pathway", Proc. Natl. Acad. Sci. USA 91:8602-8606 (1994).
Kotenko et al., "Identification of the Functional Interleukin-22 (IL-22) Receptor Complex", J. Biol. Chem. 276:2725-2732 (2001).
Kotenko et al., "Identification and functional characterization of a second chain of the interleukin-10 receptor complex", EMBO J. 16:5894-5903 (1997).
Kotenko et al., "Jak-Stat signal transduction pathway through the eyes of cytokine class II receptor complexes", Oncogene 19:2557-2565 (2000).
Kotenko et al., "The family of IL-10-related cytokines and their receptors: related, but to what extent?", Cytokine & Growth Factor Review 13 (2002) 223-240.
Sato et al., "Extracellular Signal-Regulated Kinase, Stress-Activated Protein Kinase/-Jun N-Terminal Kinase, and p38$^{mapk}$ Are Involved in IL-10-Mediated Selective Repression of TNF-α-Inducted Activation and Maturation of Human Peripheral Blood Monocyte-Derived Dendritic Cells", J. Immunol. 162:3865-3872 (1999).
Wehinger et al., "IL-10 induces DNA binding activity of three STAT proteins (Stat1, Stat3, and Stat5) and their distinct combinatorial assembly in the promoters of selected genes", FEBS Lett 394:365-370 (1996).
Xie et al., "Interleukin (IL)-22, a Novel Human Cytokine That signals through the Interferon Receptor-related Proteins CRF2-4 and IL-22R ", J. Biol. Chem. 275:31335-31339 (2000).

* cited by examiner

*Primary Examiner*—Elizabeth C. Kemmerer
(74) *Attorney, Agent, or Firm*—MH2 Technology Law Group LLP

(57) ABSTRACT

Interleukin-22 interacts with its receptor, referred to as IL-22R, and instigates a series of reactions, leading to activation of various molecules, such as JAK-1, Tyk2, and others. One can identify molecules which mediate this interaction by measuring the activity of one or more of the molecules in the pathway, to identify agonists and antagonists. These, in turn, are useful therapeutic agents, where inappropriate expression of one of the activated molecules is at issue, and requires amelioration.

6 Claims, No Drawings

METHOD FOR IDENTIFYING A SUBSTANCE WHICH MEDIATES INTERACTION BETWEEN INTERLEUKIN 22 AND AN INTERLEUKIN 22 RECEPTOR

RELATED APPLICATIONS

This application is a divisional application of application Ser. No. 10/206,274, filed Jul. 26, 2002 (abandoned), which is a continuation in part of application Ser. No. 09/915,735, filed Jul. 26, 2001 (abandoned), as well as a continuation in part of application Ser. No. 09/626,617, filed Jul. 27, 2000 (abandoned) and application Ser. No. 09/751,797, filed Dec. 29, 2000 (now U.S. Pat. No. 7,081,528), all of which are incorporated by reference.

FIELD OF THE INVENTION

This invention relates to various aspects of activation pathways involving the molecule referred to as interleukin-22, or "IL-22". In particular, it relates to methods for mediating the interaction of IL-22 and its receptors, as well as to methods for determining if IL-22 expression is occurring, has occurred, and if so, at what levels.

BACKGROUND

Interleukin-22, or "IL-22" hereafter, is an IL-10 related cytokine, that had previously been referred to as "TIF" or "IL-TIF" for "interleukin-10 related, T cell inducible factor." See U.S. Pat. Nos. 6,359,117; 6,331,613 and 6,274,710, as well as Dumoutier, et al., J. Immunol 164:1814-1819 (2000), all of which are incorporated by reference in their entirety. The molecule belongs to a family of cytokines with limited homology to IL-10, including IL-10, IL-22, mda-7/IL-24, IL-19, IL-20 and AK155/IL-26. See Moore, et al., Annu. Rev. Immunol 19:683-765 (2001); Dumoutier, et al., Eur. Cytokine Netw 13(1):5-15 (2002). The cytokine shows 22% amino acid identity with IL-10. Functionally, IL-22 activities which have been identified include upregulation of acute-phase reactants in liver and hepatoma cells (Dumoutier, et al., supra,) as well as induction of pancreatitis-associated protein (PAP 1), in pancreatic acinar cells (Aggarwal, et al., J. Interferon Cytokine Res. 21:1047-1053 (2001)), suggesting a role for the cytokine in inflammatory processes. In addition, IL-22 has been shown to induce STAT activation in several cell lines, including mesangial cells, lung and intestinal epithelial cells, melanomas, and hepatomas. See Dumoutier, et al., supra; Dumoutier, et al., Proc. Natl. Acad. Sci USA 97:10144-10149 (2000); also see patent application Ser. No. 09/626,617, filed Jul. 27, 2000, incorporated by reference which referred to "TIF" as IL-21; however, the molecule has been renamed as IL-22.

The IL-22 molecule binds at cell surfaces to a receptor complex composed of two chains, which belong to the Class II cytokine receptor family, i.e., IL-22R and IL-10Rβ. See, e.g., Dumoutier, et al., Proc. Natl. Acad. Sci USA 97:10144-10149 (2000); Xie, et al., J. Biol. Chem 275:31335-31339 (2000); Kotenko, et al., J. Biol. Chem. 276:2725-2732 (2000); also see U.S. patent application Ser. No. 09/915,735, filed Jul. 26, 2001, and incorporated by reference. This family of receptors includes receptors for type I and type II interferons, such as IFNAR1, IFNAR2, IFNGR1 and IFNGR2; IL-10Rα, IL-22R/CRF2-9, IL-10Rβ/CRF2-4, IL-20Rα/CRF2-8, IL-20Rβ/CRF2-11, and tissue factor. See Kotenko, et al., Oncogene 19:2557-2565 (2000); Blumberg, et al., Cell 104:9-19 (2001); Kotenko, Cytokine Growth Factor Rev 217: 1-18 (2002), all of which are incorporated by reference.

With the exception of IL-10R per se, signaling through the receptors for IL-10 related cytokines has not been investigated very well. The binding of IL-10 to its receptor complex (IL-10Rα and IL-10Rβ), induces activation of JAK-1, and Tyk-2 tyrosine kinases. Experiments by Finbloom et al., J. Immunol. 153:1079-1090(1995), showed that JAK-1 associates with IL-10Rα, and Tyk-2 copreciptates with IL-10Rβ. See Kotenko, et al., EMBO J 16:5894-5903 (1997), regarding Tyk-2. Activation of the two kinases, in turn, leads to phosphorylation of STAT1, 3 and 5. See Finbloom, et al., J. Immunol 153:1079-1080 (1995); Wehinger, et al., FEBS Lett 394: 365-370 (1996). In addition, IL-10 is known to activate P13 kinase, and p70S6 kinase (Crawley, et al., J. Biol. Chem 271:16357-16362 (1996)), but not the MAP kinase pathway. Indeed, Sato, et al., J. Immunol 162:3865-3872 (1999), and Geng, et al., Proc. Natl. Acad Sci USA 91:8602-8606 (1994), show that IL-10 inhibits this pathway in monocytes and dendritic cells.

The inventors have investigated the mechanism of action involved in the binding of IL-22 to its receptor, and have discovered a pathway of activation not reported previously. Since IL-22 and IL-10 share one receptor subunit, i.e., IL-10Rβ, and the functional receptor complex involves IL-22R for IL-22, and IL-10Rα for IL-10, it was believed, initially, that the signalling pathways would be nearly identical; however, this has proven to not be the case. It has now been shown that IL-22 induces phosphorylation of JAK-1 and Tyk-2, but not JAK-2. It has also been shown that JAK-1 is absolutely required for IL-22 signaling to occur. While IL-10 also activates JAK-1 and Tyk-2, and both induce phosphorylation of the same STATs, it has now been shown that IL-22 induces activation of ERK, JNK and p38 pathways, which IL-10 does not. In addition, it has been shown that IL-22 induces serine phosphorylation of STAT3, which IL-10 does not.

These, and other features of the invention will be evidenced in the disclosure which follows.

DETAILED DESCRIPTION OF PREFERRED EMBODIMENTS

Example 1

It has been established previously by, e.g., Dumoutier, et al., J. Immunol 164:1814-1819 (2000); Dumoutier, et al., Proc. Natl. Acad. Sci USA 97:10144-10149 (2000); Xie, et al., J. Biol. Chem 275:31335-31339 (2000); Kotenko, et al., J. Biol. Chem 276:2725-2732 (2000), that IL-22 induces phosphorylation of STAT1, STAT3 and STAT5. Experiments were designed to study the kinetics of phosphorylation further. Samples of rat hepatoma cell line H4IIE were grown in Iscove-Dulbecco's medium, supplemented with 10% fetal calf serum, 0.55 mM L-arginine, 0.24 mM L-asparagine, and 1.25 mM L-glutamine. Other hepatoma cell lines are known to express the IL-22R/IL-20Rβ complex, so it was presumed that H4IIE did so as well. These cells were then stimulated with recombinant murine IL-22. The recombinant murine IL-22 was produced by transiently transfecting HEK 293-EBNA human embryonic kidney cells using the well known lipofectamine method. In contrast to H4IIE, cell line HEK 293 only expresses IL-10Rβ. Supernatants from the transfected HEK293-EBNA cells (1%), were combined with $4\times10^5$ H4IIE cells, for 5, 15, or 30 minutes, or with control supernatant, for 15 minutes. Cells were lysed, in 500 μl of Laemmli buffer, and boiled for 3 minutes before loading on pre-cast, SDS-PAGE gels, and transferred, electrophoretically, to nitrocellulose membranes. The membranes were blocked in 5% non-fat dry milk, washed, and then probed with antibodies specific for phosphorylated STAT1, STAT3 and STAT5. The membranes were then reprobed with an anti actin-β antibody.

The results showed that phosphorylation of all three STAT molecules was induced within 5 minutes. Phosphorylation was transient for STAT1 and STAT5, with levels decreasing to barely detectable after 30 minutes. The phosphorylation of STAT3, however, could still be detected at least an hour after stimulation.

These experiments were repeated using recombinant murine IL-22 produced in *E. coli* in accordance with Dumoutier, et al., J. Immunol 166:7090-7095 (2001), incorporated by reference. Similar results were obtained.

Example 2

These experiments confirmed that IL-22 induced STAT phosphorylation correlated with transcriptional activation.

A total of $1.2 \times 10^7$ H4IIE cells were electroporated, at 250V, 200Ω, 1200 µF, with 50 µg pGRR5-luc, or 30 µg pSRE-luc. The pGRR5-luc construct contains 5 copies of the STAT-binding site of the FcγRI gene, inserted upstream from a luciferase gene controlled by the TK promoter. The pSRE-luc construct contains repeats of the serum responsive element of the c-fos promoter. In addition to the constructs described, supra, cells were transfected with 5 µg of reporter plasmid pRL-TK, as an internal control.

Cells were seeded in 12 well plates at $10^6$/ml. The day after plating, cells were stimulated for 3 hours with 2000 U/ml IL-22, or with control medium prior to lysis. Luciferase assays were carried out using commercially available products.

The results indicated that when cells were electroporated with the pGRR5-luc construct, IL-22 stimulation induced a 35 fold increase in luciferase activity.

Example 3

It is well know that the JAK kinases are responsible for STAT phosphorylation in response to cytokines. As such, experiments were designed to determine if JAK kinases are activated by IL-22, and if so, which of these is or are so activated.

To determine this, $5 \times 10^5$ H4IIE cells were stimulated, as described, supra, with IL-22 or control medium, and were either subjected to Western blotting, using an anti-phospho-Tyk-2 antibody, or immunoprecipitation using anti-JAK-1 or anti-JAK-2 antibodies.

With respect to Tyk-2, following Western Blot probing with the anti-phospho-Tyk-2 antibody, the membrane was re-probed, with anti-Tyk-2 antibody.

With respect to the immunoprecipitation experiments, $3 \times 10^7$ H4IIE cells were stimulated with the 1% HEK293 supernatant described supra, 250 U/ml of gamma interferon which is known to activate JAK-2 and JAK-1, or control medium, for 5 minutes. These cells were then washed, and resuspended in 1 ml of lysis buffer (1% NP-40, 0.1% deoxycholate, 0.1% SDS, 50 mM Tris, pH8, 150 mM sodium chloride, 1 mM EDTA, 1 mM sodium vanadate, 1 mM sodium fluoride, and inhibitor cocktail). Lysates were homogenized by 5 passages through a 20 gauge needle, incubated for 45 minutes on ice, and centrifuged (14,000×g). Following this, 2.5 µg of anti-JAK-1 or anti-JAK-2 polyclonal antibody were added to the supernatant, and incubated, overnight at 4° C.

The lysates were then incubated with protein A-agarose beads for two hours. The agarose beads were washed, resuspended in Laemmli buffer (25 ml), and boiled. Proteins were then separated on an 8% SDS-PAGE gel, transferred to a nitrocellulose membrane, blocked in 1% bovine serum albumin solution, and were then incubated, overnight, with 1 µg/ml of antibodies specific for phosphotyrosine. Any proteins were detected by chemiluminescence. As a control, the membranes were reprobed with anti-JAK-1 or anti-JAK-2 antibodies.

The results indicated that IL-22 stimulation of the H4IIE cells induced rapid phosphorylation of Tyk-2 and JAK-1, but not JAK-2.

Experiments were repeated using *E. coli* derived IL-22, and similar results were obtained.

Example 4

These experiments outline further assessments of the functional role of JAK-1 in IL-22 signalling.

U4C is a fibrosarcoma cell line which is known to be JAK-1 deficient. See Kohlhuber, et al., Mol. Cell. Biol 17:695-706 (1997). Samples of this cell line were transiently transfected with human IL-22R cDNA (500 ng), (Mizushima, et al, Nucleic Acids Res. 181:5322(1990)), pGRR5-luc (10 ng) and 100 ng of pRL-TK in accordance with Lejeune, et al., Biochem J. 353:109-116 (2001), incorporated by reference. Briefly, cells were seeded in 12 well plates at $4 \times 10^5$ cells/well one day prior to transfection. Standard lipofectamine methods were used. Four hours after transfection, the cells were stimulated with one of: (i) control medium, (ii) human IL-22 (2000 U/ml).

Experiments were carried out in parallel, with cultures also being transfected transiently with 40 ng of plasmid pRK5-JAK-1, which encodes JAK-1, or empty vector.

The results indicated that IL-22 failed to induce luciferase activity in the transfectants, unless the cells were transfected with JAK-1 cDNA.

Additional experiments were carried out with parental cell line 2C4, which does express JAK-1, and cell line γ2A, which is deficient in expression of JAK-2. Both cell lines were able to, and did respond to, IL-22.

Example 5

These experiments were designed to determine if IL-22 induced phosphorylation of members of the MAPK pathway. To begin, $5 \times 10^5$ H4IIE cells were seeded, in 6 well plates, one day before stimulation with recombinant, murine IL-22 (2000 U/ml), for 10, 20, 30 or 40 minutes, or with control medium for 40 minutes. In some experiments, cells were preincubated for one hour with 50 µM of a known MEK1 inhibitor, "PD98059", or 10 µM of U0126, which is also an MEK1 inhibitor. Following incubation, cell lysates were analyzed, via Western blotting as described supra, using an antiphospho-ERK1/2 antibody.

The results indicated that IL-22 induced sustained phosphorylation of ERK1/2. The inhibitors, i.e., PD98059 and U0126, both blocked phosphorylation completely. As these are both MEK inhibitors, this suggests that MEK activation is involved in phosphorylation of ERK1/2.

In follow-up experiments, Western blotting was carried out on cell lysates, in the manner described in this example, using antibodies against phosphorylated forms of MEK1/2, p90RSK, JNK/SAPK and p38, all of which are members of the MAPK pathway.

The results indicated that p90RSK was phosphorylated in response to IL-22, which is in accordance with the results, since p90RSK is a well known substrate of ERK. IL-22 also induced delayed phosphorylation of JNK/SAPK and p38 MAP kinases.

Functional activation of the MAPK pathway was confirmed by additional experiments paralleling those described supra. To elaborate, $1.2 \times 10^7$ H4IIE cells were electroporated with 30 μg of pSRE-luc, and 5 μg of pRL-TK vectors, as described supra. Cells were seeded in 12 well plates following transfection, at $10^6$ cells/well. The day after seeding, cells were preincubed for 1 hour, in the presence of DMSO (1/1000 final dilution), PD98059 (50 μM final), or U0126 (10 μM final), before stimulation with murine IL-22 (2000 U/ml), or control medium. Luciferase assays, as described supra, were carried out 3 hours after stimulation.

The data indicated that IL-22 stimulation induced a 2.25 fold increase in luciferase activity, which was abolished completely when there was preincubation with any of the MEK inhibitors.

Example 6

Follow up experiments were carried out to determine if related molecule IL-10 functioned in the same way IL-22 did.

To test this, H4IIE cells were stably transfected with IL-10Rα. This was accomplished by subcloning murine IL-10Rα cDNA into pEF/Myc/Cyto plasmid, which carries a geneticin resistance gene. A total of $1.2 \times 10^7$ H4IIE cells were electroporated (20V, 200Ω, 1200 μF), with 50 μg of IL-10Rα cDNA. The day after transfection, cells were cultured with 2 mg/ml geneticin, until a bulk culture was secured.

Following stable transfection, $5 \times 10^5$ transfected H4IIE cells were seeded in 6 well plates. One date later, the cells were stimulated with IL-1 (10 μg/ml), or murine IL-22 (2000 U/ml) for 10, 20, 30 or 40 minutes, or with control medium for 40 minutes. Total lysates were analyzed via Western blotting, with an anti-phospho-STAT3 antibody, and an anti-phospho-ERK1/2 antibody, followed by reprobing with an anti-actin-β antibody.

The IL-10 did not activate the ERK/MAPK pathway.

Example 7

The preceding examples demonstrated that STAT3 was phosphorylated in the mechanism described. STAT3 can be phosphorylated on tyrosine, but it can also be phosphorylated on a serine residue, in response to stimulation by cytokines such as IL-6. See Schuringa, et al., Biochem J 347:89-96 (2000), incorporated by reference. To determine if phosphorylation of serine was taking place, $5 \times 10^5$ H4IIE cells were seeded in 6 well plates one day before they were stimulated with murine IL-22 (2000 U/ml), for 10, 20 or 30 minutes, or with control medium for 30 minutes. Experiments were run in parallel, both with and without preincubation 1 hour prior to stimulation with 50 μM PD98059 or 10 μM U0126. Lysates were analyzed via Western blotting with an antibody specific for the serine phosphorylated form of STAT3. Reprobing of the membranes with an anti ERK1/2 antibody, and an anti-actin β antibody, followed.

Rapid serine phosphorylation was observed, with phosphorylation occurring after only 10 minutes. While it has been reported that MAPKs mediate STAT Ser phosphorylation (Schuringa, et al., supra; Decker, et al., Oncogene 19:2628-2637 (2000); Lim, et al., J. Biol. Chem 274:31055-31061 (1999)), when the H4IIE cells were preincubated with MEK inhibitors, the phosphorylation was slightly delayed, but not inhibited.

Example 8

The experiments were designed to test the functional significance of STAT3 serine phosphorylation. To test this, $1.2 \times 10^7$ H4IIE cells were electroporated with 15 ug of pGRR5-luc, 5 ug of pRL-TK, and 15 ug of a vector which encoded wild type STAT3, or a mutated form, where position 727, normally a serine residue, was replaced by alanine which prevents phosphorylation. See Schuringa, et al., FEBS Lett 495:71-76 (2001). Five hours after transfection, cells were stimulated with control medium, or murine IL-22 (2000 U/ml), for 3 hours. Luciferase assays were carried out as described, supra.

The results indicated that the mutation at position 727 reduced luciferase induction from an 8-fold to a 4-fold increase upon IL-22 stimulation, suggesting strongly that STAT3 serine phosphorylation is required for maximum activation.

To further investigate STAT3 serine phosphorylation, the effect of the STAT3 Ser727Ala mutant was tested on IL-10 induced transactivation. The IL-10 based experiments were carried out because IL-10 has never been described to phosphorylate STAT3 on a serine residue. To test this, $4 \times 10^5$ HEK 293 cells were seeded in 12 well plates. The day after, these cells were transfected, either with a vector encoding human IL-22R (500 ng) or one encoding murine IL-10Rα (500 ng), using the standard lipofectamine method. The cells were also transfected with a plasmid encoding the wild type STAT3 (1 ug) or the Ser727Ala mutant form of STAT3 (1 ug) together with 100 ng pGRR5-luc, 100 ng pRL-TK reporter plasmids and empty vector to give a total plasmid DNA content of 2 ug. Five hours after transfections, cells were stimulated with control medium, human IL-22 (2000 U/ml) or human IL-10 (10 ng/ml) for 24 hours. Luciferase assays were carried out as described, supra.

Simultaneously, cells were stimulated with IL-22, IL-10 or control medium for 15 minutes before the lysis. The concentration of the stimulating agents was as described, supra.

Western blotting was carried out with total lysates, using antibodies which detected either serine phosphorylated or tyrosine phosphorylated STAT3. Membranes were reprobed with anti-actin β antibodies.

The results indicated that IL-22 stimulation of the IL-22R transfected HEK293 cells resulted in a 6.5 fold increase in luciferase activity. Cotransfections with the STAT3 mutant reduced the activity to 4 fold. In contrast, the cotransfection of the STAT3 mutant into cells expressing IL-10R had no effect on IL-10 induced transactivation. Further, Western blot analysis showed that IL-22, but not IL-10, induced STAT3 serine phosphorylation while both induced tyrosine phosphorylation of STAT3.

The preceding examples establish that the binding of IL-22 to a receptor leads to activation of STAT1, 3 and 5, as well as the activation of various kinases, including JAK-1, Tyk-2, MEK1/2, p90RSK, JNK/SAPK and p38. Activation of STAT3 requires phosphorylation of tyrosine; however, when STAT3 is phosphorylated on tyrosine, it can be further activated by serine phosphorylation. Hence, one embodiment of the invention is a method for screening to determine if a compound of interest mediates the effect of IL-22, especially the effect of IL-22 on a cell. This method involves, inter alia, combining the compound of interest with IL-22 or a portion of IL-22 sufficient to bind to an IL-22 receptor, and a cell which expresses both an IL-22 receptor and at least one molecule which is activated as a result of the interaction between IL-22 and its receptor, determining if said compound is activated, if so, the degree of activation, and comparing the value obtained to a control value, wherein any difference there between indicates that the compound of interest mediates the interaction between IL-22 and the receptor. In this way, both antagonist and agonists can be determined.

The IL-22 used may be prepared recombinantly, which is preferred, or may have been prepared via purification from naturally occurring sources. The IL-22 may be IL-22 from any species which produces it, preferably mammal, such as murine IL-22, and most preferably, human IL-22.

When produced recombinantly, the IL-22 may be produced via expression in prokaryotic cells, such as *E. coli*, or eukaryotic cells, such as the HEK293 cells, as is discussed supra; however, the skilled artisan will appreciate that other host cells may be used, as can cell free transcription systems.

While the whole IL-22 molecule may be used, portions of an IL-22 molecule which posses the ability to bind to an IL-22 receptor may be used. The determination of whether or not a portion of an IL-22 molecule can be used in the assays of the invention can be determined very easily, such as by way of any of the assay mechanisms described in the preceding examples, or any other method known to the skilled artisan. Also, variants of IL-22 which contain one or more amino acid additions, deletions, or substitutions, but which retain the ability to bind to a receptor may be used.

The determination of whether or not a interaction of IL-22 and a receptor compound is mediated can be measured in any number of ways. For example, it was shown, supra, that the induction of STAT phosphorylation correlates with transcription regulation. Hence, one way to determine if a compound mediates the interaction of IL-22 and an IL-22 receptor is to measure the level of transcription of a substance that is mediated by a STAT molecule, such as STAT1, STAT3, and/or STAT5. Such nucleic acid based assays may be carried out using methods well known in the art. For example, one may use oligonucleotide probes specific to one or more of the genes whose transcription is mediated by one of the STAT molecules, such as STAT1, 3 and/or 5, and determine the amount of hybridization of the probes. The probes may be labelled, such as with a radiolabel, a calorimetric label, a biotin molecule, or any of the labels well known as nucleic acid "markers." Also, one could subject the transcripts to any of the well known amplification assays, such as PCR, LCR and so forth. Of course, one could also use an assay of the type described supra, wherein a reporter molecule is recombined into the cell, where expression of the reporter molecule is dependent upon the phosphorylated expression of one or more STAT molecules. Similarly, while full length receptor molecules may be used, so can; truncated forms of these molecules, as well as modified forms which present one or more amino acid additions, deletions, or substitutions, but which nonetheless maintain their ability to bind to IL-22 or an IL-22 fragment or variant.

In addition to, or instead of the molecules mediated by STAT molecules, one may measure phosphorylation levels of kinases, such as JAK-1 and/or Tyk-2, as well as the member of the MAPK family described herein, including, but not being limited to, ERK1/2, MEK1/2, p90RSK, JNK/SAPK and/or p38, whose phosphorylation, activity and ability to induce additional expression is upregulated by IL-22. Any combination of these molecules may be measured on the phosphorylation level.

In addition to, or as an alternative to, the DNA based assays described, supra, one may assay for the interaction described supra via an immunoassay. As noted, the levels of phosphorylation of STAT1, 3, 5, JAK-1, Tyk-2, ERK1/2, MEK1/2, p90RSK, JNK/SAPK and/or p38 may be measured. One may use antibodies which bind specifically to one or more of these molecules, but more preferably one uses antibodies which specifically bind to activated forms of these molecules such as phosphorylated forms. More specifically, one can use immunoassays which target tyrosine phosphorylation of the target molecules, and in the case of STAT3 for example, serine phosphorylation.

Any of the standard immunoassays will known to the art may be used, including western blotting, as described supra, radioimmunoassays, enzyme linked immunosorbent assays, precipitation assays, assays involving solid phase/liquid phase separation, and so forth.

Similarly, i.e., STAT1, 3, 5, JAK-1, Tyk-2, ERK1/2, MEK1/2, p90RSK, JNK/SAPK and p38 all have specific well defined functions in cells, one may measure a feature directly or indirectly influenced thereby, as a measure of the interaction.

In this way, any of the various methods can be used to determine agonists or antagonists of IL-22 or IL-22 receptors, such as antibodies, antibody fragments, IL-22 replacements, and so forth.

As was shown, supra, while the effects of IL-22 and IL-10 overlap somewhat, there are differences. These differences may be expiated in, e.g., determining if an individual, a cell type, a population of cells, etc., is under or overexpressing IL-22 or IL-10. For example, it was shown, supra, that IL-22 is involved in phosphorylation of serine residues in STAT3, while IL-10 is not. Hence, by specifically determining a feature such as the level of serine phosphorylation in STAT3, one can determine if IL-22 is being over an underexpressed.

Also a feature of the invention is a method for determining the length of time after which a cell has been exposed to IL-22 or a receptor binding fragment, as it has been determined that while certain molecules are phosphorylated immediately, but that the phosphorylated forms decrease remarkable fast, others maintain phosphorylation for extended periods of time. Hence, if e.g., STAT1 and/or STAT3 are present in phosphorylated form, then either stimulation with IL-22 is ongoing, or has taken place recently. In contrast, presence of high concentrations of phosphorylated STAT3 need not indicate that stimulation was recent.

The examples also indicate that JAK-1 is critical for efficacy of IL-22. This suggests another embodiment of the invention, which is a method to modify effect of IL-22 on a cell, either by adding JAK-1 thereto or a portion of the JAK-1 molecule which interacts with complexes of IL-22 and an IL-22 receptor, or by adding a JAK-1 inhibitor which prevents the JAK-1 molecule from interacting in the manner described supra. This modulators of JAK-1 function may act on the protein level, or may act on the transcription, such as promating or inhibiting phosphorylation. Similarly, mediators of the IL-22/IL-22R binding described herein may be used as therapeutic agents, to treat subject's suffering from conditions characterized by inappropriate expression of the molecules in the pathways described herein, including the STAT molecules, JAK-1, Tyk-2, MEK1/2, p90RSK, JNK/SAPK, and p38. These antagonists or agonists can be administered in manners well known to the art and need not be reiterated here.

Other features of the invention will be clear to the skilled artisan and need not be reiterated further.

We claim:

1. A method for identifying a substance which mediates binding between interleukin-22 (IL-22) and an interleukin-22 receptor (IL-22R), comprising:
   a) admixing IL-22 or an IL-22R binding fragment thereof, a cell which presents an IL-22R or an IL-22 binding fragment thereof on its surface, and said substance, b) determining activation of a molecule that is expressed by said cell, said molecule selected from the group consisting of STAT1, STAT5, JAK-1, Tyk2, ERK1/2, MEK1/2, p90RSK, JNK/SAPR and p38, and c) comparing activation of said molecule to activation when said cell is admixed with IL-22 or an IL-22R binding fragment thereof in the absence of said substance, any differences therebetween indicating said substance mediates said binding.

2. The method of claim 1, comprising determining said activation via an immunoassay.

3. The method of claim 1, comprising determining said activation via measuring nucleic acid expression of said molecule.

4. The method of claim 2, wherein said immunoassay comprises an assay using an antibody which binds specifically to a phosphorylated form of said molecule.

5. The method of claim 1, comprising determining said expression via a hybridization assay.

6. The method of claim 3, comprising determining said activation by transfecting or transforming said cell with a nucleic acid molecule which generates a detectable signal upon activation of said molecule selected from the group consisting of STAT1, STAT5, JAK-1, Tyk2, ERK1/2, MEK1/2, p90RSK. JNK/SAPR and p38.

* * * * *